United States Patent
Tschulena et al.

(10) Patent No.: US 10,525,187 B2
(45) Date of Patent: Jan. 7, 2020

(54) APPARATUS FOR REMOVING PROTEIN-BOUND TOXINS FROM BLOOD PLASMA

(71) Applicant: Fresenius Medical Care Deutschland GmbH, Bad Homburg (DE)

(72) Inventors: Ulrich Tschulena, Frankfurt (DE); Joachim Jankowski, Stahnsdorf (DE); Anselm Fabig, Zeuthen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 864 days.

(21) Appl. No.: 14/653,399

(22) PCT Filed: Dec. 19, 2013

(86) PCT No.: PCT/EP2013/003867
§ 371 (c)(1),
(2) Date: Jun. 18, 2015

(87) PCT Pub. No.: WO2014/095072
PCT Pub. Date: Jun. 26, 2014

(65) Prior Publication Data
US 2015/0306298 A1    Oct. 29, 2015

Related U.S. Application Data

(60) Provisional application No. 61/740,648, filed on Dec. 21, 2012.

(30) Foreign Application Priority Data

Dec. 21, 2012   (DE) .................. 10 2012 025 164

(51) Int. Cl.
*A61M 1/34*     (2006.01)
*A61M 1/36*     (2006.01)
(Continued)

(52) U.S. Cl.
CPC ............ *A61M 1/3486* (2014.02); *A61M 1/16* (2013.01); *A61M 1/1601* (2014.02); *A61M 1/34* (2013.01);
(Continued)

(58) Field of Classification Search
None
See application file for complete search history.

(56) References Cited

U.S. PATENT DOCUMENTS 2,698,622 A * 1/1955 Martens ................... A61N 1/40
                                                              331/175
5,628,727 A * 5/1997 Hakky ................ A61M 1/3681
                                                               604/20

(Continued)

FOREIGN PATENT DOCUMENTS

CN    2290349    9/1998
CN    2294782    10/1998
(Continued)

OTHER PUBLICATIONS

Vanholder et al. "Review on uremic toxins: Classification, concentration, and interindividual variability" Kidney International, vol. 63 (2003), pp. 1937-1943.
(Continued)

*Primary Examiner* — Krishnan S Menon
*Assistant Examiner* — Brad Gordon
(74) *Attorney, Agent, or Firm* — Jacobson Holman, PLLC.

(57) ABSTRACT

The invention relates to an apparatus for extracorporeal removal of protein-bound toxins from blood plasma comprising a first line device, a second line device, a third line device and a fourth line device, a dialyzer or hemofilter arranged between the first line device and the second line device and/or an adsorber, means for generating a field, at
(Continued)

Figure 1:
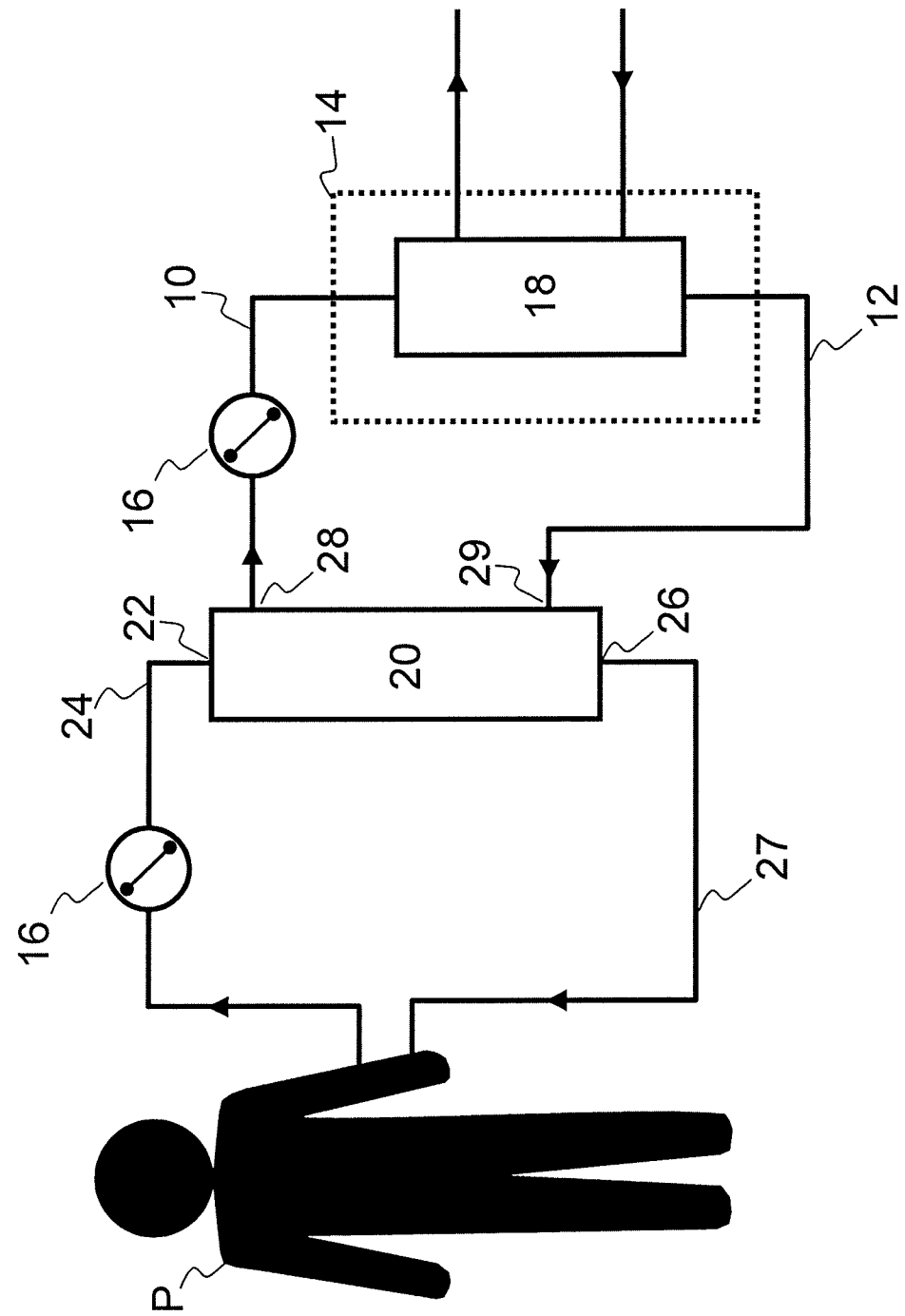

least partially surrounding the first line device and/or the dialyzer or hemofilter and/or the adsorber, a controllable fluid conveyance device arranged in the first line device and/or the second line device, and at least one controllable body fluid conveyance unit arranged in the third line device and/or the fourth line device, a filter, wherein the permeate side of the filter is connected to the first line device and the second line device, and the side of the filter to be dialyzed is connected at its inlet to the third line device, which can be connected to a patient and is connected at its outlet to the fourth line device which can be connected to the patient, wherein a controllable flow of fluid through the line devices and the dialyzer or hemofilter and/or the adsorber can be generated by means of the fluid conveyance devices.

13 Claims, 12 Drawing Sheets

(51) Int. Cl.
*A61M 1/16* (2006.01)
*B01D 15/08* (2006.01)
*B01D 63/00* (2006.01)
*B03C 1/02* (2006.01)

(52) U.S. Cl.
CPC ........ *A61M 1/3472* (2013.01); *A61M 1/3482* (2014.02); *A61M 1/3618* (2014.02); *A61M 1/3679* (2013.01); *A61M 1/3681* (2013.01); *B01D 15/08* (2013.01); *B01D 63/00* (2013.01); *B03C 1/02* (2013.01); *A61M 2202/0415* (2013.01); *A61M 2202/0445* (2013.01); *A61M 2202/07* (2013.01); *A61M 2205/054* (2013.01); *A61M 2205/33* (2013.01); *A61M 2205/3317* (2013.01); *A61M 2205/3324* (2013.01); *A61M 2205/75* (2013.01)

(56) References Cited

U.S. PATENT DOCUMENTS

| | | |
|---|---|---|
| 2002/0182738 A1 | 12/2002 | Connelly et al. |
| 2003/0187380 A1 | 10/2003 | Botto et al. |
| 2005/0010163 A1* | 1/2005 | Aoki ................. A61N 1/40 604/20 |
| 2005/0015040 A1* | 1/2005 | Wuepper ............ A61M 1/3472 604/5.01 |
| 2005/0082225 A1 | 4/2005 | Kreymann |
| 2009/0259160 A1 | 10/2009 | Josephs |
| 2010/0217172 A1* | 8/2010 | Hyde ................. A61M 1/3679 604/5.01 |
| 2014/0246367 A1 | 9/2014 | Jankowski et al. |

FOREIGN PATENT DOCUMENTS

| | | |
|---|---|---|
| CN | 1322146 | 11/2001 |
| CN | 102549439 | 7/2012 |
| EP | 1434645 | 7/2004 |
| EP | 2087916 | 8/2009 |
| EP | 2446908 | 5/2012 |
| RO | 122077 | 12/2008 |
| WO | WO 03/020403 | 3/2003 |
| WO | WO 03/094998 | 11/2003 |
| WO | WO 2007/044642 | 4/2007 |
| WO | WO 2008/108980 | 9/2008 |
| WO | WO 2013004604 | 1/2013 |

OTHER PUBLICATIONS

Polaschegg et al. "Hemodialysis machines and monitors", Replacement of Renal Function by Dialysis, Drukker, Parsons, and Maher, Kluwer Academic Publishers, 4. Edition 1996, pp. 333-379.

* cited by examiner

APPARATUS FOR REMOVING PROTEIN-BOUND TOXINS FROM BLOOD PLASMA

The present invention relates to an apparatus for removing protein-bound toxins from the blood plasma of patients under the influence of an electromagnetic alternating field and/or an electric DC field.

The task of a healthy kidney is to eliminate end products from the metabolism (substances that must be removed in urine) and toxins (uremic toxins) from the body by forming urine. The kidney removes a broad spectrum of substances of different molecular weights. A review of uremic toxins was published by R. Vanholder et al. (R. Vanholder et al., *Kidney International*, 63 (2003) 1934-1943). Uremic toxins are classified in three classes on the basis of their molecular weight. Toxins with a molecular weight of less than 500 Dalton form the group with a low molecular weight. The medium-sized molecules are in a middle range with a molecular weight between 500 and 12,000 D. The medium-sized molecules include for example $\beta_2$-microglobulin (11,800 D). The third class of uremic toxins is formed by molecules with a molecular weight of more than 12,000 D.

In addition, uremic toxins are also differentiated according their water solubility. Examples of uremic toxins with a good water solubility and a low molecular weight include urea, creatinine, oxalates, guanidine and uric acid.

Examples of uremic toxins with a low water solubility include p-cresol, indoxyl sulfate, phenol, hippuric acid and homocysteine. These uremic toxins are primarily bound to proteins in the serum.

In a healthy person, uremic toxins are eliminated with the urine via the kidneys. In chronic renal failure, however, uremic toxins remain in the patient's blood and must be removed by hemodialysis or peritoneal dialysis.

Although it is readily possible to remove water-soluble toxins such as urea or creatinine using the known dialysis methods, for example hemodialysis, removing hydrophobic uremic toxins which have a low water solubility is very difficult by hemodialysis methods due to the protein binding. It is assumed in general that a chemical equilibrium is established between the free dissolved toxin and the protein-bound toxin, and this equilibrium is shifted to the side of the protein-bound toxin. This means that most of these uremic toxins are bound to proteins and only a small portion remains dissolved in the blood plasma.

Many of these substances are low molecular components, only a small percentage of which is present in free form, so in principle they can be dialyzed.

It is also assumed that plasma proteins, in particular albumin, function as a bond partner of the hydrophobic uremic toxins. Albumin is retained by dialysis membranes because of its molecular weight. Thus albumin is not removed by hemodialysis methods. Therefore only the free dissolved portion of the uremic toxins can be removed from a patient's blood. The establishment of the equilibrium under dialysis becomes the rate-determining step. Although it is expected that after removal of the dissolved toxins from the blood, the equilibrium between free and protein-bound toxins will be reestablished again, and if the dialysis time is long enough, a substantial portion of the toxins can be removed, but this time is not available in hemodialysis treatments.

Thus there is a demand for dialysis methods which also remove the protein-bound uremic toxins from the patient's blood.

The object of the present invention is thus to provide a novel apparatus for removing protein-bound toxins from blood plasma. Furthermore, another object of the present invention is to provide a corresponding method.

The present invention relates to an apparatus according to the preamble of Claim 1 for removing protein-bound toxins from the blood plasma of patients under the influence of a high-frequency electric or electromagnetic alternating field and/or an electric DC field.

According to the invention the apparatus comprises a first extracorporeal circulation to receive blood for purification and a second circulation having a hemodialyzer and/or hemofilter. The two circulations are connected via a filter, in particular a plasma filter or a cell separator which has a filtered side and an unfiltered side. The unfiltered side is separated from the filtered side by at least one filter material, for example a filter membrane, wherein a liquid supply inlet on the unfiltered side is connected to a third line device that can be connected to the patient, a liquid removal outlet on the unfiltered side is connected to a fourth line device that can be connected to the patient, a liquid removal outlet on the filtered side is connected to the first line device and a liquid supply inlet on the filtered side is connected to a second line device. Thus the first line device can be connected to the patient via the third line device, and the second line device can be connected to the patient via the fourth line device. The plasma filter preferably has a pressure gradient so that filtration is performed in the front area of the filter (transfer of liquid from the unfiltered side to the filtered side); filtration is performed there and refiltration is performed in the rear area of the filter (transfer of liquid from the filtered side to the unfiltered side), i.e., the purified blood plasma is returned to the patient. As an alternative to a plasma filter, a cell separator may also be installed for separation of blood into plasma and cellular constituents. This cell separator may be a centrifuge, for example.

The filter can retain the cellular components of the blood, where albumin and other plasma proteins with the uremic toxins bound to them and other small molecular substances can be allowed to pass through with the blood plasma. The plasma protein-toxin complex can thus enter the first line device, the uremic toxins can be removed and the purified blood plasma can then be returned to the patient via the second and/or fourth line devices.

An electromagnetic alternating field and/or an electric DC field may act on the side of the filtrate containing the plasma as well as on the side of the enriched liquid. Irradiation on the side of the filtrate containing the plasma offers the advantage that the electromagnetic alternating field and/or the electric DC field does not act on the blood cells. This further increases the biocompatibility of this method.

The blood plasma is purified through an adsorber and/or a dialyzer or hemofilter.

Furthermore, the apparatus has means for generating a high-frequency electric or electromagnetic alternating field and/or a device for generating an electric DC field, wherein the blood to be purified is exposed to the high-frequency electromagnetic alternating field and/or to the electric DC field before and/or during its contact with the adsorber or the dialyzer/hemofilter. The present invention thus makes available a method which shifts the position of the equilibrium between free and protein-bound toxins and accelerates the establishment of an equilibrium during the dialysis treatment.

The invention is based on the finding that the bonds between uremic toxins and plasma proteins are not usually "true" chemical (covalent) bonds but instead are reversible bonds. These bonds are based essentially on the electrostatic properties and interactions of the molecules involved. It has been found that the strength of these bonds or interactions can be reduced according to the invention by the action of high-frequency electric or electromagnetic fields. By using high-frequency electric electromagnetic fields and/or electric DC fields during dialysis, the proportion of protein-bound uremic toxins can be reduced significantly. As part of the dialysis performed in everyday clinical practice, the rate of release of protein-bound uremic toxins from the protein binding can be increased by additional application of high-frequency electric or electromagnetic fields and/or electric DC fields. This improves the separation of these substances from the patient's blood during dialysis. The respective uremic toxins can thus be dialyzed more effectively and to a greater extent.

Methods of hemodialysis and hemofiltration are familiar to those skilled in the art. A summary of the most important hemodialysis methods and machines can be found in the publications "Replacement of Renal Function by Dialysis" (Drukker, Parsons and Maher; Kluwer Academic Publishers, 4th edition 1996; and "Hemodialysis Machines and Monitors" by H.-D. Polaschegg and N. W. Levin)—the disclosure content of which is herewith explicitly referenced. In hemodialysis a patient's blood is passed through an arterial bloodline into the blood chamber of a dialyzer. The blood is normally conveyed with the help of a peristaltic rotary pump arranged in the arterial bloodline. After passing through the pump, the blood is passed through the blood chamber of the dialyzer and finally through a venous drip chamber and a venous bloodline connected thereto and returned to the patient. A venous pressure monitor is connected to the venous drip chamber as a protective system for directly detecting any blood loss to the environment. If necessary, the two needles required for arterial and venous cannulas may be replaced by a single needle in the so-called single-needle dialysis. In this type of dialysis, the extracorporeal circulation consists of a single-needle cannula with a connected Y piece. The venous line leads from the dialyzer back to the Y piece. The venous and arterial lines are sealed off in alternation by clamps. One or more blood pumps are provided to ensure alternating flow to and from the Y-piece.

In hemodialysis, the dissolved substances are removed from the blood by diffusion through the dialyzer membrane. Although a slight additional transmembrane pressure is applied for ultrafiltration of the excess water from a patient, this filtration hardly plays any role in the purification of blood to remove specific substances.

In hemofiltration, dissolved substances are removed by convection but not diffusion. At the same time, the ultrafiltrate is replaced almost completely by a substitution fluid having a composition similar to that of the dialysate in dialysis. In this method similarity to the natural kidney and more effective removal of larger molecules are emphasized. However, the removal of low-molecular substances is reduced in comparison with hemodialysis because at most 45% of the blood can be ultrafiltered in so-called postdilution hemofiltration.

Hemodiafiltration, which is a combination of hemodialysis and hemofiltration, can be performed by combining the extracorporeal circulations of a hemofiltration machine and a hemodialysis machine. Hemodialysis machines with volumetrically controlled ultrafiltration can easily be adapted for hemodiafiltration, which is less expensive. It is especially inexpensive when the substitution fluid is prepared online from the dialysis fluid.

In summary it can be stated that in hemodialysis the patient's blood is purified by the fact that the substances to be removed from the blood diffuse through the membrane of the dialyzer because of a concentration gradient and thereby reach the dialysis fluid. The driving force in hemofiltration is essentially a pressure difference across the membrane which causes a convective transport of substances through the membrane and thereby purifies the blood of higher molecular substances in particular. In hemofiltration and in the combined method of hemodiafiltration, fluid is removed from the patient's blood and must be replaced except for a small differential amount to control the fluid balance.

The apparatus according to the invention may also have an adsorber in or downstream from the means for generating a high-frequency electromagnetic alternating field and/or a device for generating an electric DC field. This adsorber may be for example an anion exchanger or a nonspecific adsorber. Whereas the anion exchanger binds bilirubin, bile acids and other ions, the non-specific adsorber, for example a neutral resin or activated carbon may retain other protein-bound toxins.

The apparatus according to the invention as defined in the preamble of Claim 1 additionally has means for generating a field. The field may be a high-frequency electric field, a high-frequency electromagnetic field, a magnetic field and/or an electric DC field. Those skilled in the art are familiar with means for generating such fields.

The apparatus according to the invention may have for example a high-frequency capacitor, a high-frequency coil and/or a high-frequency electrode for generating a high-frequency electric or electromagnetic field. The high-frequency electric field or the high-frequency electromagnetic field has a frequency of 100 kHz to 2 GHz, preferably 1 MHz to 1 GHz. For example a high-frequency electromagnetic field having a magnetic flux density of less than or equal to 100 mTesla, preferably of 0.001 to 100 mTesla, especially preferably from 0.01 to 10 mTesla, in particular from 0.01 to 2 mTesla may be used.

To release the bond between the plasma protein and the uremic toxin, a high-frequency electric or electromagnetic field is used according to the invention. The high-frequency electromagnetic field may have a frequency of 100 KHz to 1 GHz, preferably from 0.5 MHz to 100 MHz, especially preferably for 1 MHz to 50 MHz, most especially preferably from 1 MHz to 20 MHz. The blood to be purified may be exposed to a high-frequency electric or electromagnetic field which has essentially a constant frequency over time. Alternatively the high-frequency electric or electromagnetic field may have a varying frequency such that the frequency and/or field strength may be buried in a regular or irregular pattern. In one exemplary embodiment the blood to be purified is exposed to a high-frequency electromagnetic field which begins at a relatively low frequency and whose frequency is increased over time up to a previously defined maximum frequency. As an alternative to this the blood to be purified may also be exposed to a high-frequency electric or electromagnetic field which begins at a high maximum frequency and whose frequency is reduced over time to a previously determined minimum frequency. Through the use of a high-frequency electromagnetic field with varying frequencies, the efficacy of releasing the bonds between uremic toxin and plasma protein can be improved.

In addition, the apparatus according to the invention may have means for generating an electric DC field. Those skilled in the art are familiar with such apparatuses. The apparatus according to the invention may be constructed of a plate capacitor having two, four or more plates for example. The electric DC field has a field strength of up to 1500 V/m. In a preferred embodiment the electric DC field has a field strength of 10 V/m to 400 V/m, especially preferably 100 V/m to 250 V/m.

The means for generating a high-frequency electric or electromagnetic field, a magnetic field and/or an electric DC field may be designed and arranged in and/or on the blood plasma circulation in such a way that the blood plasma to be purified may be exposed to the field before, during or both before and during the contact of the blood plasma to be purified with the dialyzer (18) and/or with the adsorber (19).

In a preferred embodiment of the apparatus according to Claim 1, means for generating a high-frequency electric or electromagnetic field are used.

In another preferred embodiment of the apparatus according to Claim 1, means for generating a high-frequency electric or electromagnetic field and means for generating an electric DC field are used.

A line device (24 and 27) that can be connected to the patient may be connected directly to the patient. Alternatively optional other line devices may also be provided by which the patient is in fluid connection with the line devices (24 and 27).

The body-fluid-conveying device (16) can be controlled with regard to its fluid flow rate and can thus generate a regulable flow rate of body fluid and/or fluid through the apparatus. The fluid delivery rate is in a range from 100 to 500 mL/min. In a preferred embodiment it is approx. 300 mL/min. The body fluid conveyance device may be a pump, for example a diaphragm pump or a peristaltic pump.

Protein-bound toxins are also eliminated in the liver in particular. It is therefore also conceivable to use the apparatus according to the invention in the treatment of acute or chronic hepatic failure.

Figure 2:
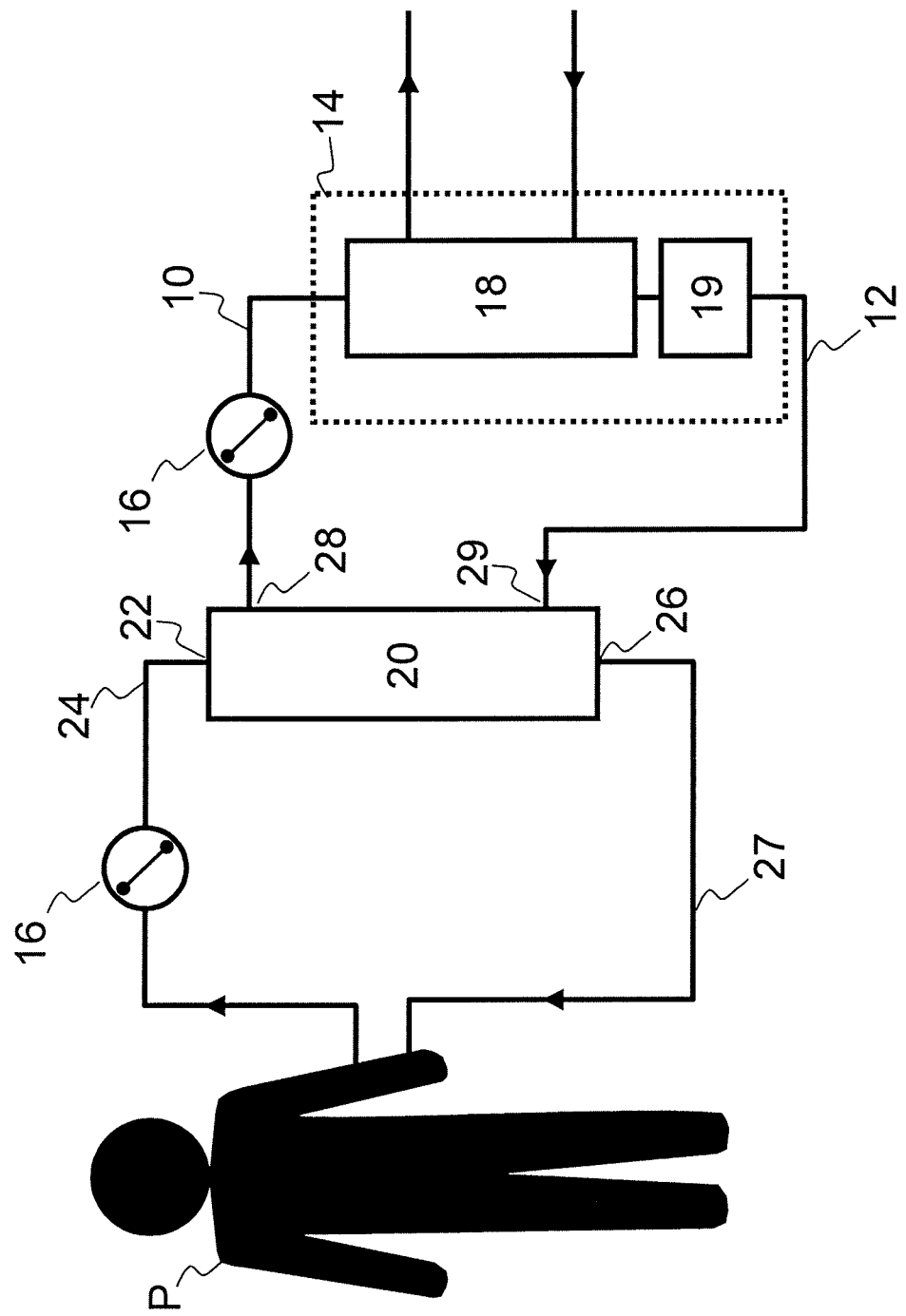
Figure 3:
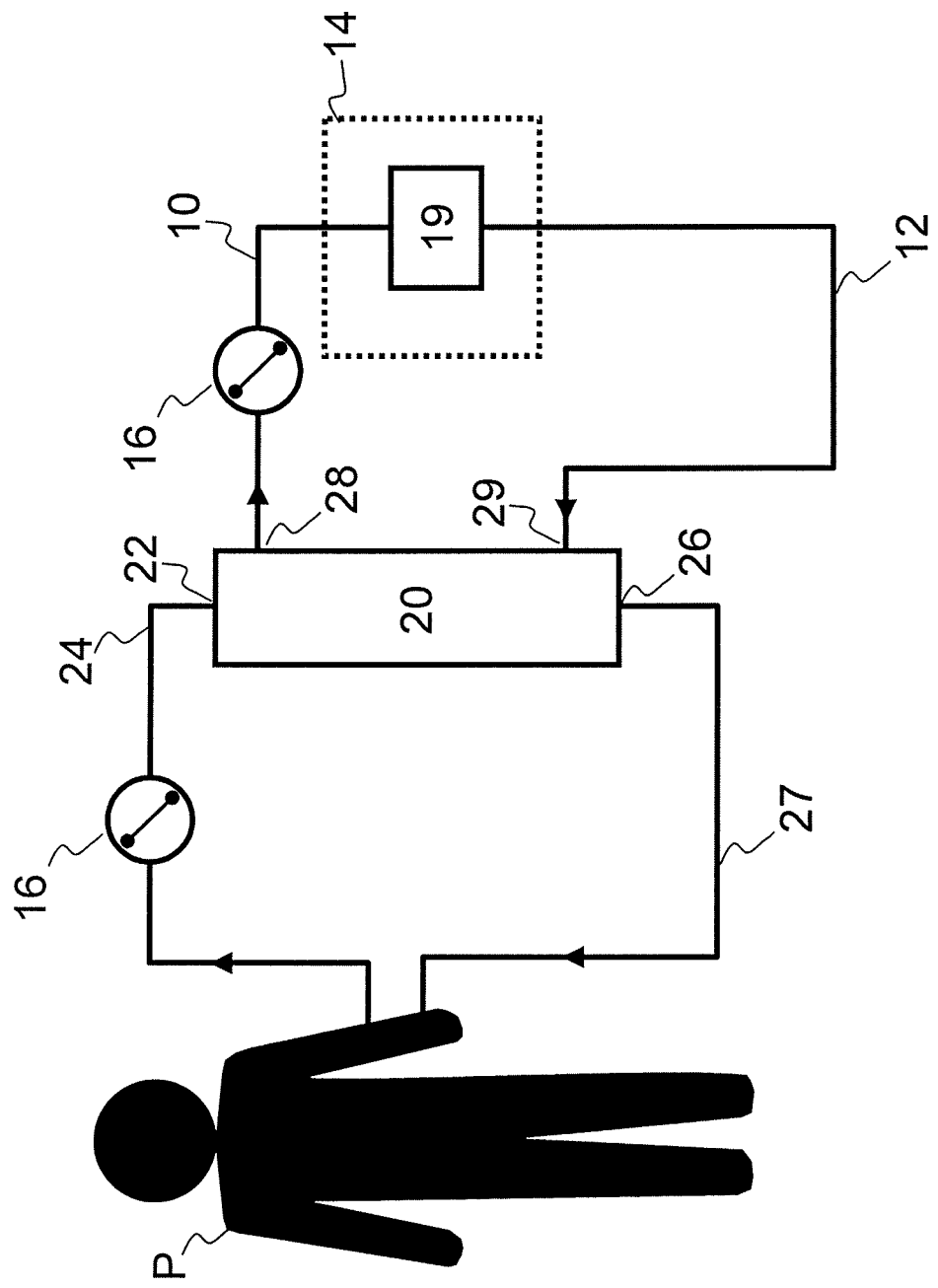
Figure 4:
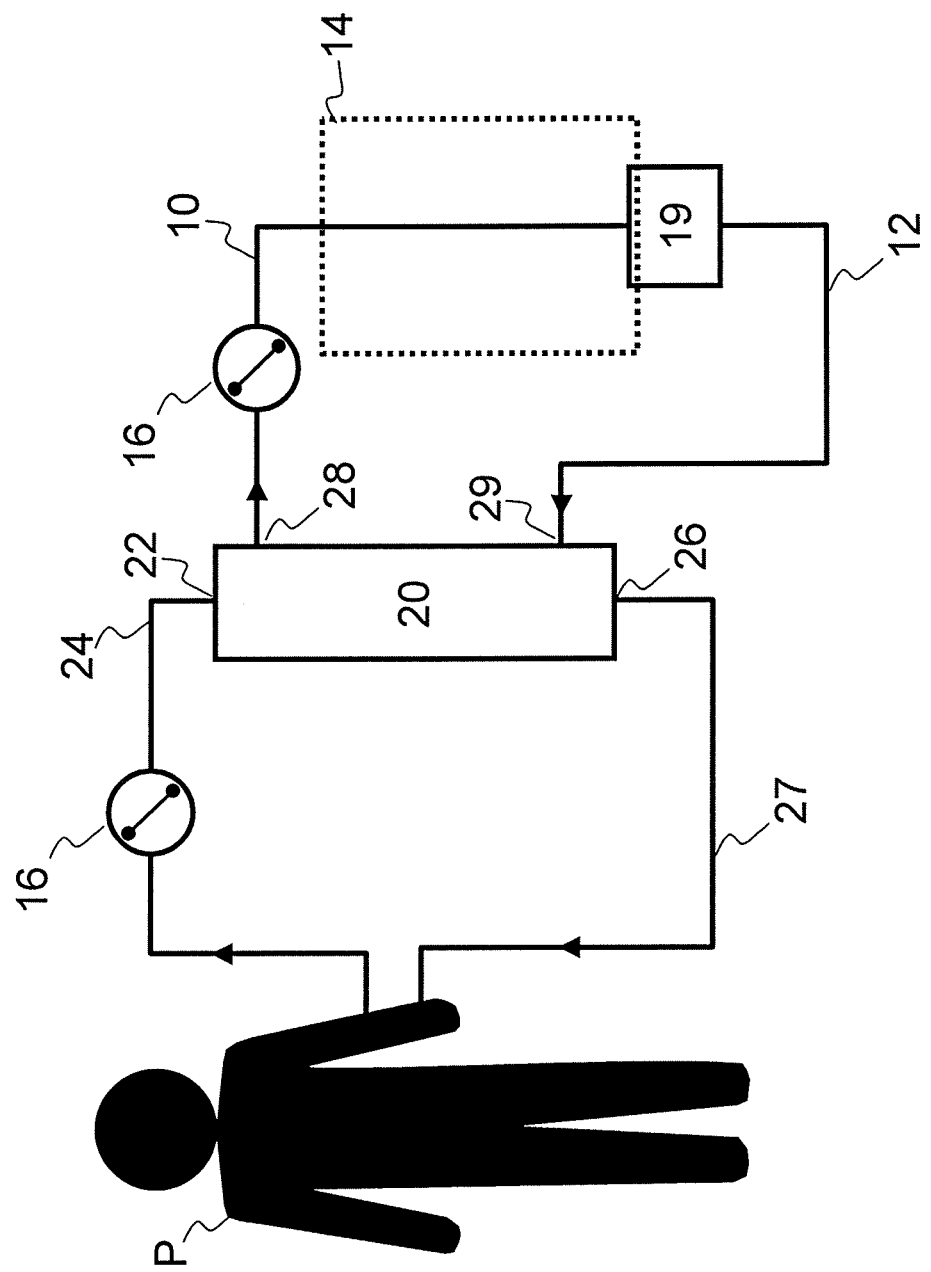
Figure 5:
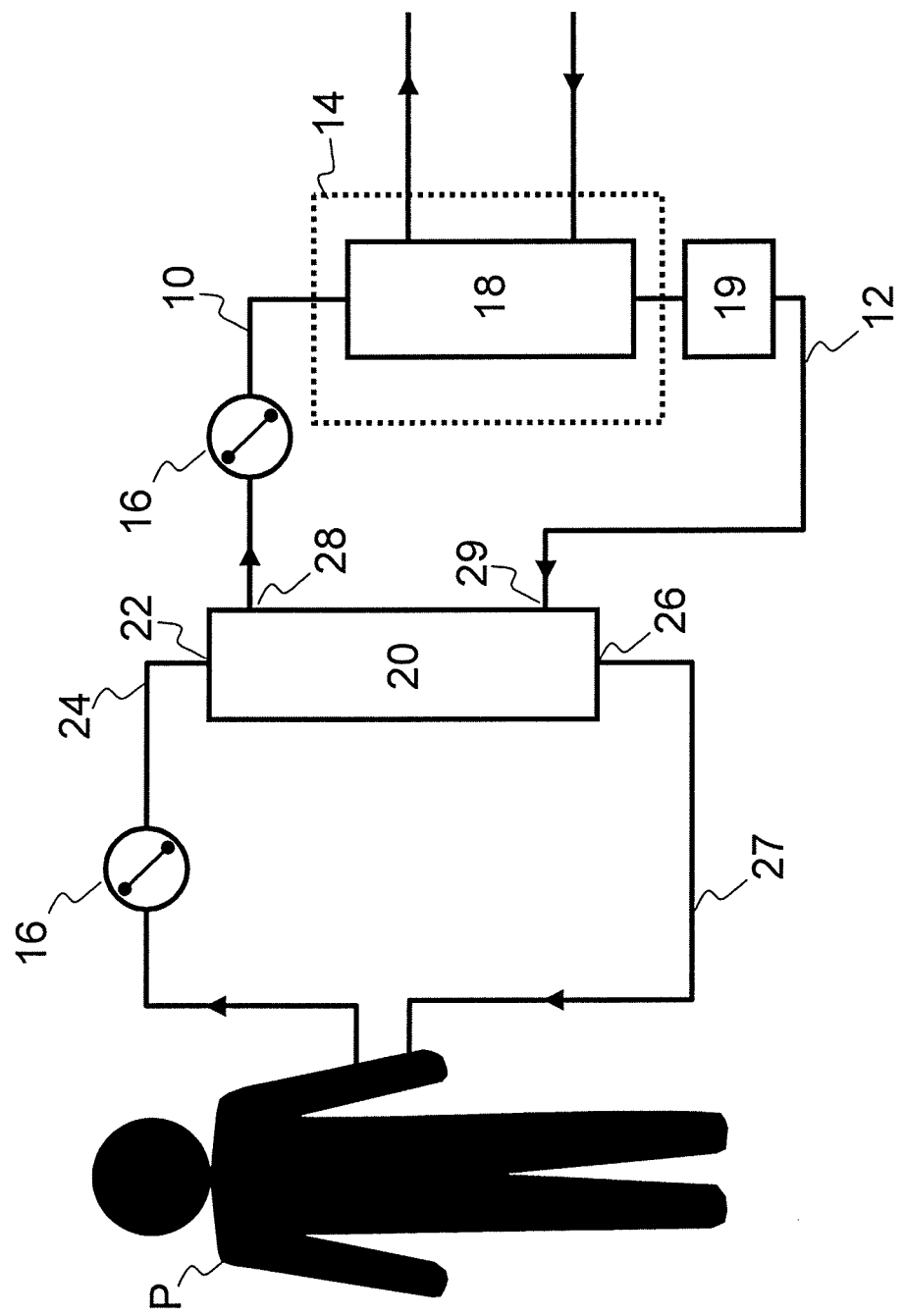
Figure 6:
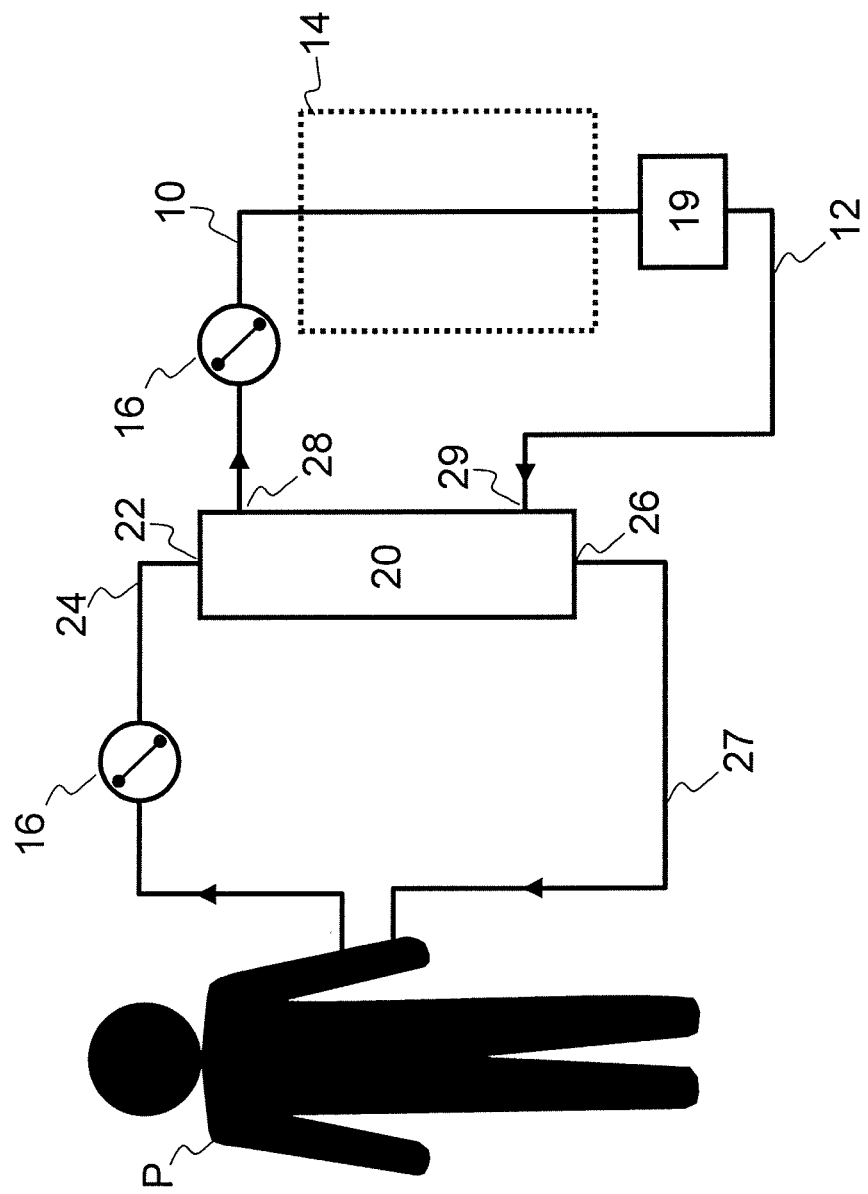
Figure 7:
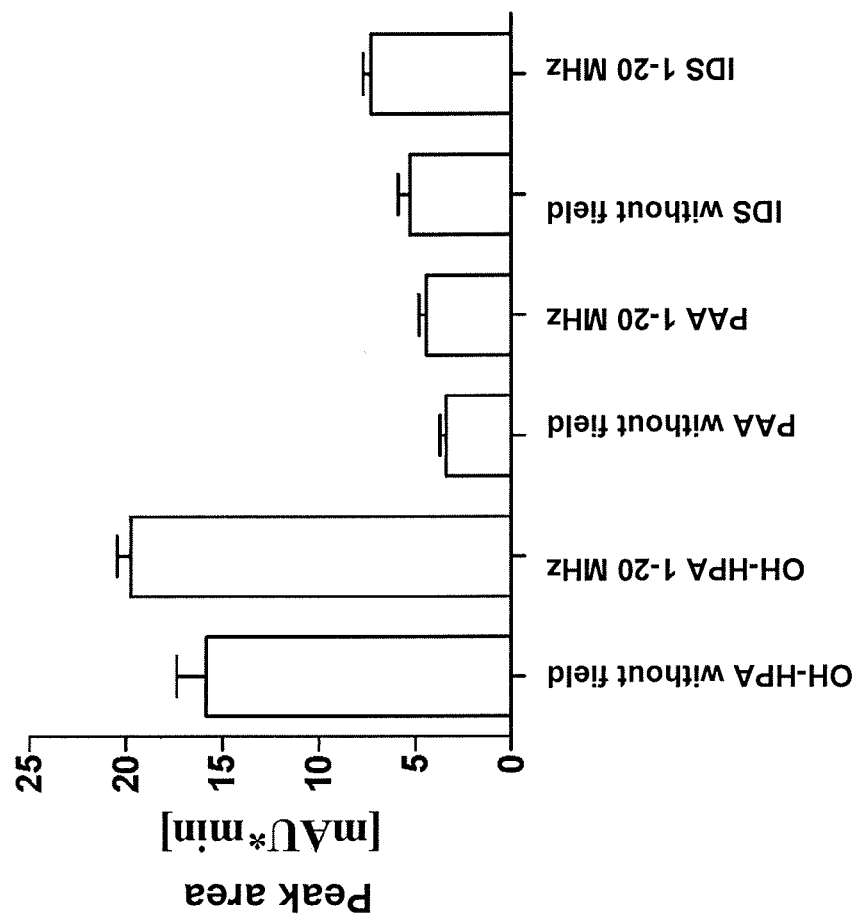
Figure 8:
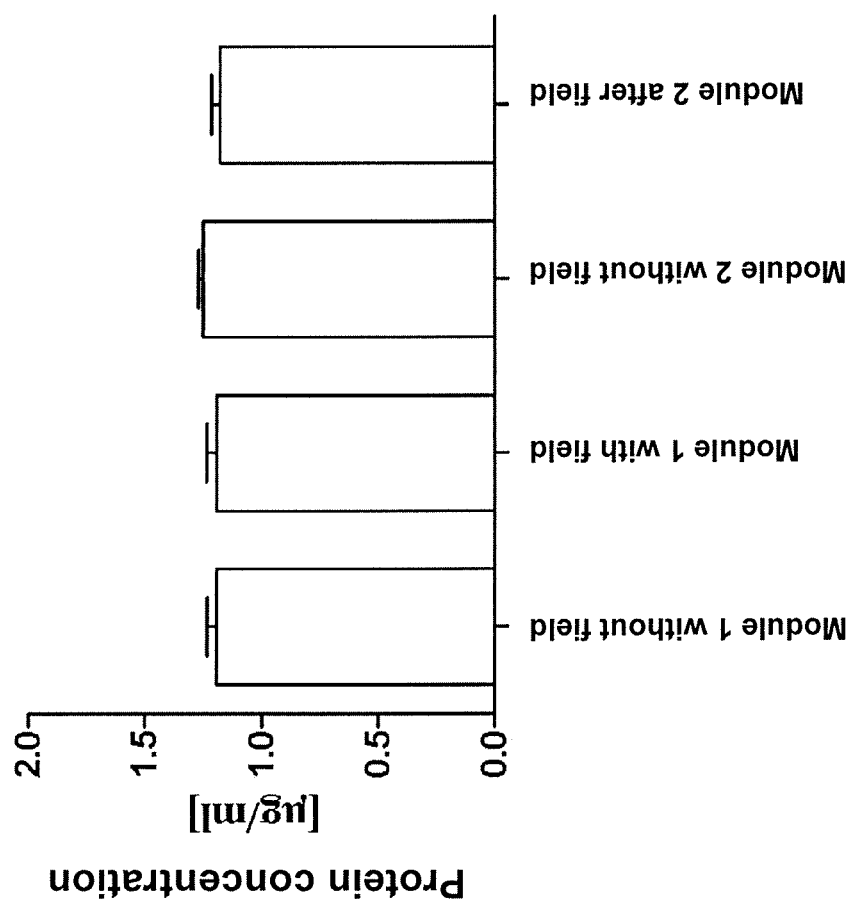
Figure 9:
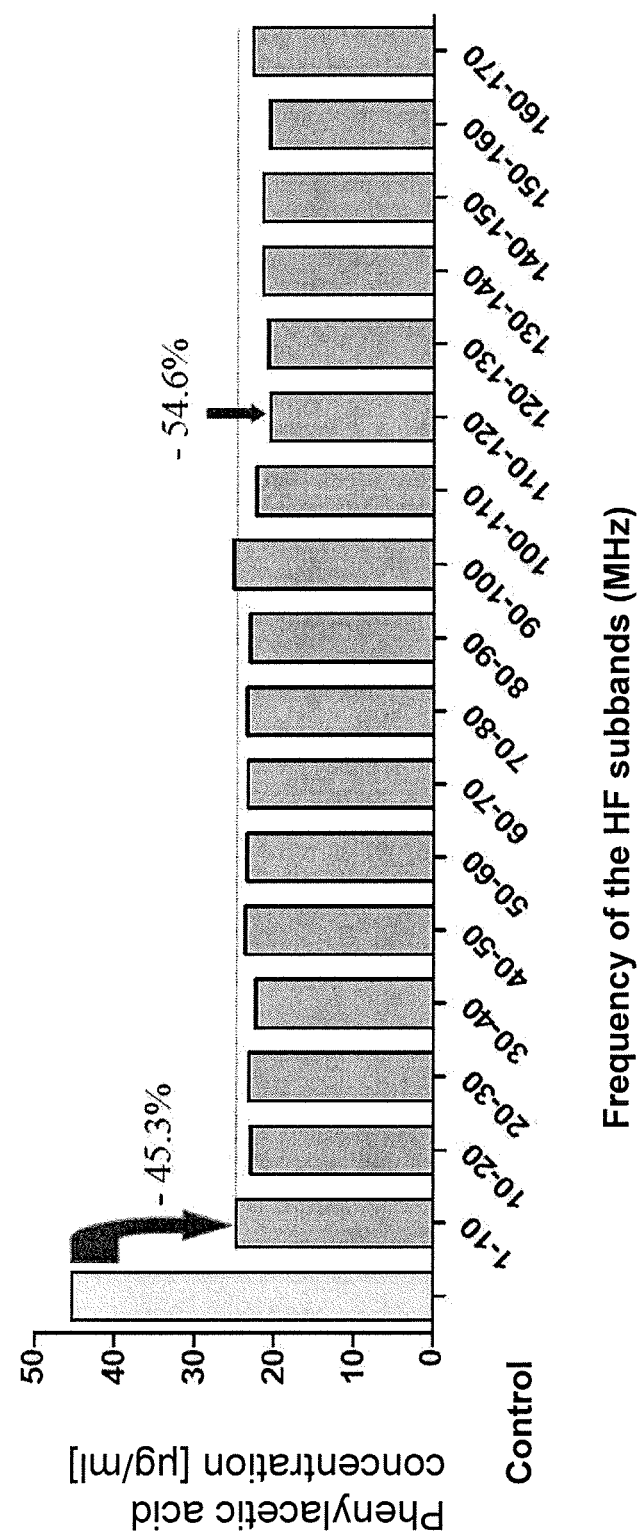
Figure 10:
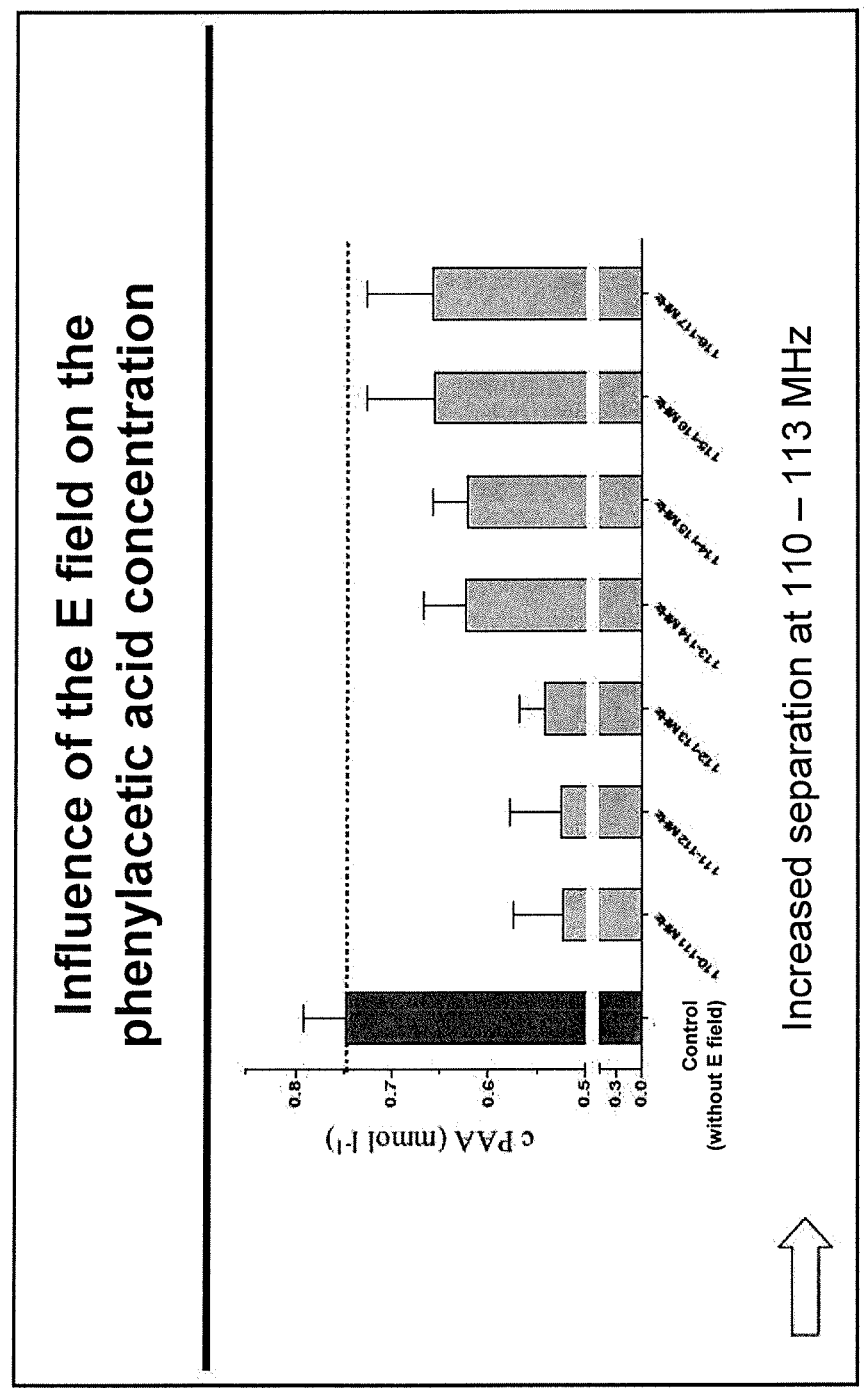
Figure 11:
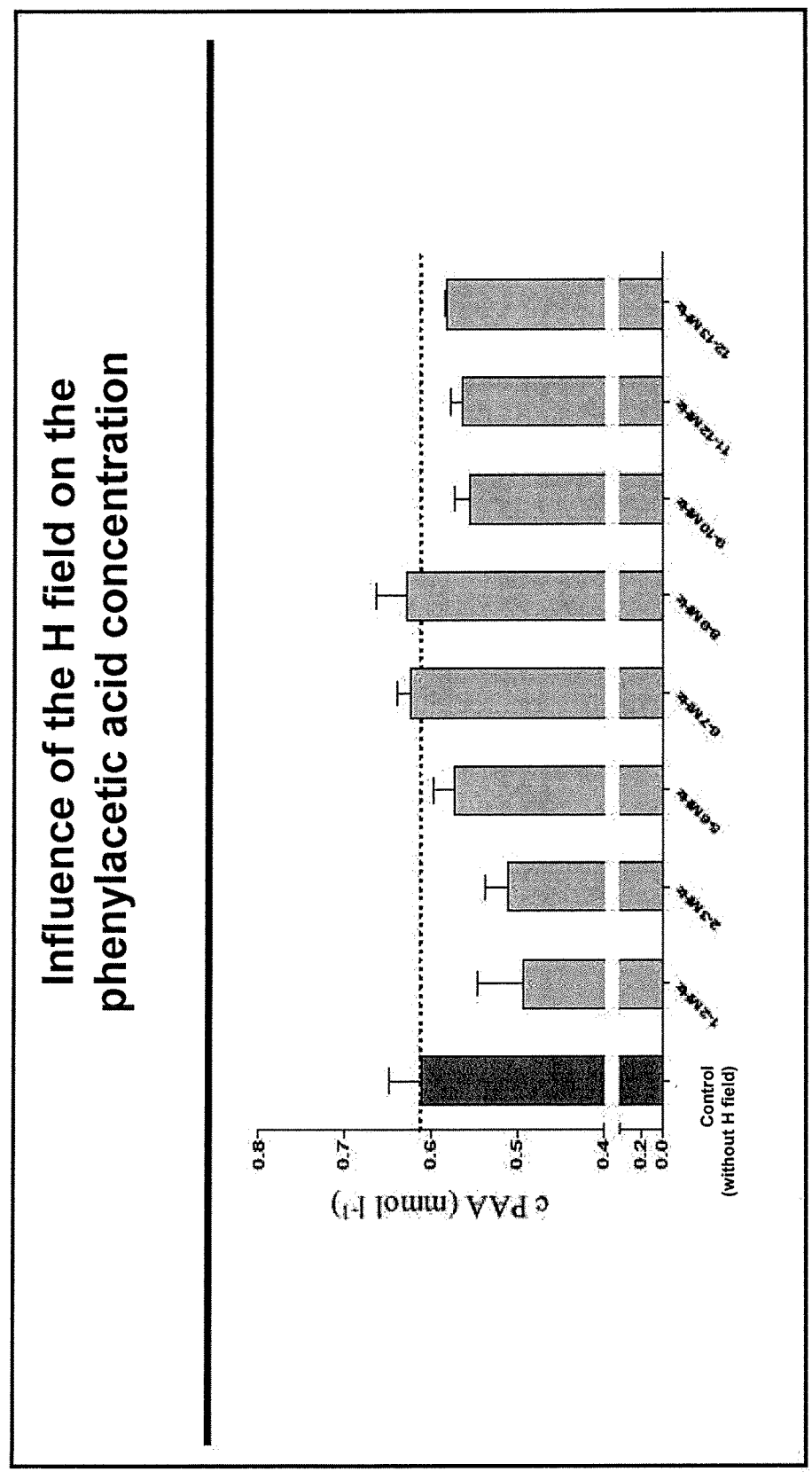
Figure 12:
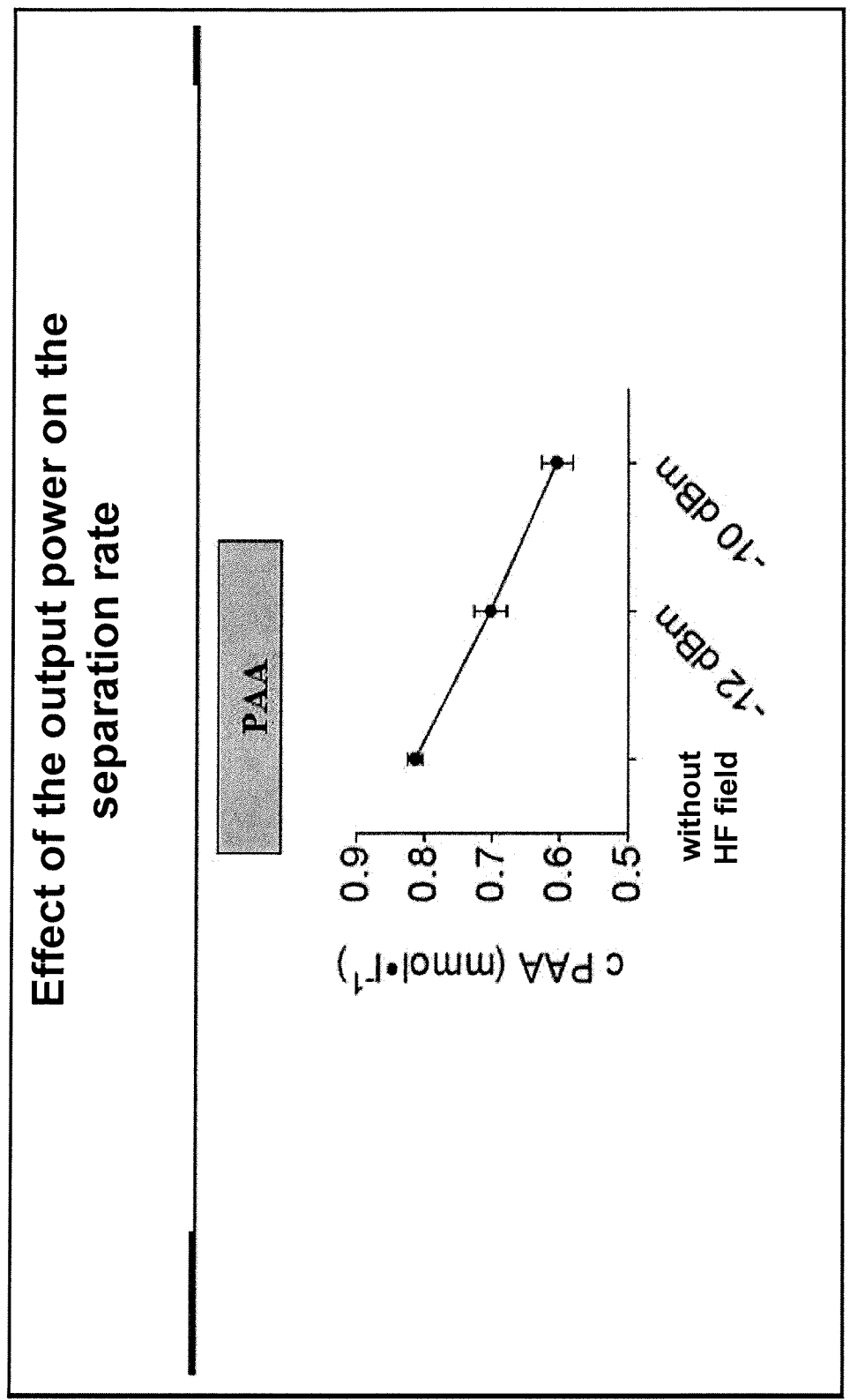

Further details and advantages of the invention result with reference to the Figures and embodiments explained in the following. There are shown in the Figures:

FIG. 1: a schematic block diagram of an embodiment of an apparatus in accordance with the invention;

FIG. 2: a schematic block diagram of a further embodiment of the apparatus in accordance with the invention;

FIG. 3: a schematic block diagram of a further embodiment of the apparatus in accordance with the invention;

FIG. 4: a schematic block diagram of a further embodiment of the apparatus in accordance with the invention;

FIG. 5: a schematic block diagram of a further embodiment of the apparatus in accordance with the invention;

FIG. 6: a schematic block diagram of a further embodiment of the apparatus in accordance with the invention;

FIG. 7: experimental results relating to the influence of high-frequency electromagnetic fields on the protein-bound portion of uremic toxins;

FIG. 8: experimental results as proof of the lack of damage to the membrane by the high-frequency fields;

FIG. 9: experimental results relating to the influences of an HF field in the frequency range 1 to 170 MHz on the protein-bound portion of uremic toxins;

FIG. 10: experimental results relating to the influences of an HF field in the frequency range 110 to 115 MHz on the protein-bound portion of uremic toxins;

FIG. 11: experimental results relating to the influences of an HF field in the frequency ranges 1 to 6 MHz and 9 to 13 MHz on the protein-bound portion of the uremic toxins; and FIG. 12: experimental results relating to the influences of the field strength on the protein-bound portion of the uremic toxins.

FIG. 1 shows schematically one embodiment of the apparatus according to the invention. The reference numerals of this Figure are associated as shown below:
10 first line device,
12 second line device,
14 means for generating a field,
16 liquid conveyance device,
18 hemodialyzer or hemofilter with inlet and outlet lines for a dialysis fluid,
20 filter/cell separator,
24 third line device,
27 fourth line device,
22 liquid inlet on the unfiltered side,
26 liquid outlet on the unfiltered side
28 liquid outlet on the filtered side and
29 liquid inlet on the filtered side,
P patient A third line device 24 has a first end and a second end, such that the first end can be connected to the patient P and the second end is connected to the fluid inlet 22 of the unfiltered side of a filter 20. In addition to the unfiltered side, the plasma filter 20 has a filtered side, such that the unfiltered side is separated from the filtered side by at least one filter material. The fourth line device 27 has a first end and a second end, such that the first end is connected to the fluid outlet 26 of the unfiltered side of a filter 20, and the second end can be connected to the patient P. Whole blood entering through the fluid inlet 22 on the unfiltered side can emerge again as blood plasma partially through the fluid outlet 28 on the filtered side. Then the blood plasma that has been separated is passed through the first line device 10 through a dialyzer 18 which is at least partially surrounded by means for generating a field 14. Under the influence of the field, the protein-bound toxins are at least partially released and are separated through the membrane of the dialyzer 18. Next the irradiated and purified blood plasma flows through the second line device 12 and re-enters the plasma filter 20 at the fluid inlet 29 on the filtered side and emerges into the fourth line device through the fluid outlet 26 on the unfiltered side. Thus the unfiltered whole blood and the irradiated and purified blood plasma are recombined in the fourth line device 27 and are returned to the patient P.

FIG. 2 shows schematically another embodiment of the apparatus according to the invention. Parts identical with the above-described embodiment are marked by identical reference numerals. In addition, an adsorber 19 is located downstream from the dialyzer (18) within the field 14 in this embodiment of the apparatus in accordance with the invention.

The third line device 24 in accordance with the embodiment shown in FIG. 2 has a first end and a second end, where the first end can be connected to the patient P and the second end is connected to the fluid inlet 22 on an unfiltered side of a filter 20. In addition to the unfiltered side, the plasma filter 20 has a filtered side, such that the unfiltered side is separated from the filtered side by at least one filter material. The fourth line device 27 has a first end and a second end, such that the first end is connected to the fluid outlet 26 on the unfiltered side of a filter 20, and the second end can be connected to the patient P. Whole blood entering through the fluid inlet 22 on the unfiltered side can emerge again as blood plasma partially through the fluid outlet 28 on the filtered side. Then the separated blood plasma is passed via the first line device 10 through a dialyzer 18 and an adsorber 19, both of which are at least partially surrounded by means for generating a field 14. Under the action of the field, the protein-bound toxins are at least partially released and are separated via the membrane of the dialyzer 18. Then the blood plasma flows further through the adsorber 19 which picks up the toxins released in the field. Next the blood plasma flows into the second line device 12 and enters the plasma filter 20 at the fluid inlet 29 on the filtered side and emerges into the fourth line device through the fluid outlet 26 on the unfiltered side. Thus unfiltered whole blood and irradiated and purified blood plasma come in contact with one another again in the fourth line device 27. This apparatus has the advantage that in addition to the dialyzer 18, an adsorber 19 which binds the toxins released from the plasma proteins is also provided. The arrangement of the adsorber 19 in the plasma circulation has the additional advantage that adsorber material released from the adsorber is retained by the plasma filter and cannot enter the whole blood circulation (24, 27).

FIG. 3 shows schematically one embodiment of the apparatus according to the invention. Parts identical with the above-described embodiments are marked by identical reference numerals. In this embodiment of the apparatus in accordance with the invention, an adsorber 19 is located within the field 14 instead of the dialyzer 18.

The third line device 24 in accordance with the embodiment shown in FIG. 3 has a first end and a second end, such that the first end can be connected to the patient P and the second end is connected to the fluid inlet 22 on the unfiltered side of a filter 20. In addition to an unfiltered side, the plasma filter 20 also has a filtered side, such that the unfiltered side is separated from the filtered side by at least one filter material. The fourth line device 27 has a first end and a second end, such that the first end is connected to the fluid outlet 26 on the unfiltered side of a filter 20, and the second end can be connected to the patient P. Whole blood, which can enter through the fluid inlet 22 on the unfiltered side, can emerge again as blood plasma partially through the fluid outlet 28 on the filtered side. Then the separated blood plasma is passed via the first line device 10 through an adsorber 19, which is at least partially surrounded by means for generating a field 14. Under the action of the field, the protein-bound toxins are at least partially released and are picked up by the adsorber 19. Next the irradiated and purified blood plasma passes through the second line device 12 and enters the blood plasma filter 20 again at the fluid inlet 29 on the filtered side and emerges through the fluid outlet 26 on the unfiltered side into the fourth line device 27 through the fluid outlet 26. The unfiltered whole blood and the irradiated and purified blood plasma are thus brought back together again in the fourth line device 27.

FIG. 4 shows schematically one embodiment of the apparatus according to the invention. Parts identical with the above-described embodiments are marked by identical reference numerals. The adsorber 19 is located downstream partially outside the field 14 in this embodiment of the apparatus in accordance with the invention.

The third line device 24 in accordance with the embodiment shown in FIG. 4 has a first end and a second end, such that the first end can be connected to the patient P and the second end is connected to the fluid inlet 22 on the unfiltered side of a filter 20. In addition to the unfiltered side, the plasma filter 20 also has a filtered side, such that the unfiltered side is separated from the filtered side by at least one filter material. The fourth line device 27 has a first end and a second end, such that the first end is connected to the fluid outlet 26 on the unfiltered side of a filter 20, and the second end can be connected to the patient P. Whole blood entering through the fluid inlet 22 on the unfiltered side can emerge again as blood plasma partially through the fluid outlet 28 on the filtered side. Then the separated blood plasma is passed via the first line device 10 through an adsorber 19 which is only partially surrounded by means for generating a field 14. Under the action of the field, the protein-bound toxins are at least partially released and are picked up by the adsorber 19. Next the irradiated and purified blood plasma flows through the second line device 12 and enters the plasma filter 20 again at the fluid inlet 29 on the filtered side and emerges through the fluid outlet 26 on the unfiltered side into the fourth line device 27. Thus unfiltered whole blood and the irradiated and purified blood plasma are brought together again in the fourth line device 27.

FIG. 5 shows schematically another preferred embodiment of the apparatus according to the invention. Parts identical with the above-described embodiments are marked by identical reference numerals. In addition, an adsorber 19 is located downstream from the dialyzer (18) outside the field 14 in this embodiment of the apparatus in accordance with the invention.

The third line device 24 in accordance with the embodiment shown in FIG. 5 has a first end and a second end, such that the first end can be connected to the patient and the second end is connected to the fluid inlet 22 of the unfiltered side of a filter 20. In addition to the unfiltered side, the plasma filter 20 also has a filtered side, such that the unfiltered side is separated from the filtered side by at least one filter material. The fourth line device 27 has a first end and a second end, such that the first end is connected to the fluid outlet 26 on the unfiltered side of a filter 20 and the second end can be connected to the patient P. Whole blood which enters through the fluid inlet 22 on the unfiltered side can leave again as blood plasma partially through the fluid outlet 28 on the filtered side. Then the separated blood plasma is sent through the first line device 10 through a dialyzer 18 and an adsorber 19. In this embodiment only the dialyzer 18 is at least partially surrounded by means for generating a field 14. Under the action of the field, the protein-bound toxins are at least partially released and are separated across the membrane of the dialyzer 18. Next the blood plasma flows through the adsorber 19 again, where the toxins released in the field are adsorbed. Next the blood plasma flows into the second line device 12 and enters the plasma filter 20 again at the fluid inlet 29 on the filtered side and emerges again through the fluid outlet 26 on the unfiltered side into the fourth line device. Thus the unfiltered whole blood and the irradiated and purified blood plasma are combined again in the fourth line device 27. This apparatus has the advantage that in addition to the dialyzer 18, an adsorber 19 additionally binds the toxins released from the plasma proteins. The arrangement of the adsorber in the plasma circulation (10, 12) has the additional advantage that adsorber material released from the adsorber is retained by the plasma filter and cannot enter the whole blood circulation (24, 27).

FIG. 6 shows schematically another embodiment of the apparatus according to the invention. Parts identical with the above-described embodiments are marked by identical reference numerals. The electric field 14 acts on the first line device 10 in this embodiment of the apparatus in accordance with the invention. An adsorber 19 is located downstream, outside the field 14.

The third line device 24 in accordance with the embodiment shown in FIG. 6 has a first end and a second end, such that the first end can be connected to the patient P and the second end is connected to the fluid inlet 22 on the unfiltered side of a filter 20. In addition to the unfiltered side, the plasma filter 20 also has a filtered side, such that the unfiltered side is separated from the filtered side by at least one filter material. The fourth line device 27 has a first end and a second end, such that the first end is connected to the fluid outlet 26 on the unfiltered side of the filter 20 and the second end can be connected to the patient P. The whole blood which enters through the fluid inlet 22 on the unfiltered side can emerge again as blood plasma partially through the fluid outlet 28 on the filtered side. Then the separated blood plasma is sent through an adsorber via the first line device 10. In this embodiment only the first line device 10 is at least partially surrounded by means for generating a field 14. Under the influence of the field the protein-bound toxins are at least partially released. Next the blood plasma flows further through the adsorber 19 which picks up the toxins released in the field. Next the blood plasma flows into the second line device 12 and enters the plasma filter 20 again at the fluid inlet 29 on the filtered side and then emerges through the fluid outlet 26 on the unfiltered side into the fourth line device. In the fourth line device 27, thus the unfiltered whole blood and the irradiated and purified blood plasma are combined again. In this embodiment, the arrangement of the adsorber in the plasma circulation (10, 12) again has the advantage that adsorber material released from the adsorber is retained by the plasma filter and cannot enter the whole blood circulation (24, 27).

The following experimental results serve as experimental proof of the effect of an electric field on the separation of protein-bound toxins during the dialysis.

The effect of an HF field in the frequency range from 1 to 20 MHz is described in embodiment 1. Embodiment 2 shows the effect of the HF field in the frequency range from 1 to 170 MHz on the separation of phenylacetic acid. The separation rate for phenylacetic acid was able to be increased by at least 45.3% under the influence of the HF field. The effect was particularly pronounced at 54.6% in the subband from 110 to 120 MHz. The subband from 110 to 120 MHz is looked at more closely in embodiment 3. Embodiment 4 shows the influence of an H field in the ranges 1-6 MHz and 9-13 MHz. Embodiment 5 shows the influence of the field strength on the separation of phenylacetic acid.

The temperature was kept constant in all embodiments 1 to 5 so that the observed changes are based on the properties of the electric field and not on a heating.

Embodiment 1

The influence of high-frequency electromagnetic fields on the protein-bound portion of the uremic toxins was examined in a series of in vitro experiments.

A dialysis module was set up for this purpose in that conventional hemofiltration capillaries were cast as loops using silicone into a syringe receiving neck. An aqueous albumin solution was introduced into the respective module in the presence of the uremic toxins phenylacetic acid, p-hydroxyhippuric acid and indoxyl sulfate. This solution was filtered with the dialysis module using a syringe pump for 10 min. A high-frequency electromagnetic field was subsequently induced in the solution by using a high-frequency electrode (HF electrode). The electromagnetic field is incremented by means of a high-frequency voltage source over a period of 10 minutes from 1 to 20 MHz in steps of 1 MHz. The concentration of the uremic toxins phenylacetic acid, p-hydroxyhippuric acid and indoxyl sulfate previously added to the artificial plasma was determined in the resulting filtrates. The effect of the HF field on the bond between the proteins and the uremic toxins was able to be evaluated by a comparison of the uremic toxin concentration in the resulting filtrates.

The quantitative determination of the uremic toxin concentration in the resulting filtrates showed that high-frequency electromagnetic fields significantly increase the filtration rates of the protein-bound uremic toxins (FIG. 7). The protein concentration in the filtrate was determined using Bradford protein dyeing to check whether high-frequency electromagnetic fields damage the dialysis membranes. The results show that no significant changes of the protein concentration can be detected in dialysis modules without and with the influence of high-frequency electromagnetic fields (FIG. 8). Macroscopic damage to the membrane can be precluded on the basis of these data.

Embodiment 2

Examination of the HF field effect in the frequency range 1 to 170 MHz.

An aqueous solution of bovine serum albumin (BSA, 60 mg/ml) was introduced into the dialysis module of Example 1 in the presence of the uremic toxin phenylacetic acid (1 mmol/l in 0.9% NaCl solution). The HF field was varied in subbands of 10 MHz in the frequency range 1-170 MHz and was compared with a control experiment without an HF field.

The quantitative determination of the phenylacetic acid was performed using HPLC.

The results of the experiments are collected in FIG. 9. The separation rate for phenylacetic acid was able to be increased by at least 45.3% under the influence of the HF field. The effect was particularly pronounced at 54.6% in the subband from 110 to 120 MHz.

Embodiment 3

This embodiment follows on from the examinations in accordance with Embodiment 2 which showed that the effect was particularly pronounced in the subband from 110 to 120 MHz.

In the continuing examinations in accordance with Embodiment 3, the frequency range about 110 to 115 MHz was in particular able to be identified as an effective frequency range for the release of protein-bound uremic toxins. FIG. 10 shows the respective effect on the corresponding release and the subsequent separation of phenylacetic acid.

According to the current status, the frequency ranges named summarily in Table 1 are suitable for the separation of protein-bound uremic toxins.

TABLE 1

| Suitable frequencies in the HF field | | | |
| --- | --- | --- | --- |
| Frequencies E Field | PAA | IDS | pCRS |
| 80-120 MHz | 110 110-111 111 | 110 110-111 111 | 110 110-111 111 |
| 120-170 MHz | 140-141 148-149 160-161 | 140-141 | 140-141 151-152 |

The respective frequency ranges are the ranges at which the maximum separation effect was determined. An increased separation was determined in part in the non-named frequency ranges in comparison with the control; however, it was smaller than in the named frequency ranges.

Embodiment 4

An increased release and thus separation of the protein-bound uremic toxins was furthermore also able to be determined in the region of the H field.

It can be seen from FIG. 11 that the H field range from 1-6 MHz and the range 9-13 MHz are suitable to release protein-bound uremic toxins from the protein bond and consequently to separate them dialytically. The effect on phenylacetic acid is shown in FIG. 11.

Embodiment 5

In addition to the frequency of the field used, its field strength is also relevant to the resulting release and separation. As the field strength increases, the respective uremic toxins are increasingly released from the protein bond and are subsequently separated.

FIG. 12 shows the effect of an increasing field strength on the content of protein-bound uremic toxins in the retentate for the example of phenylacetic acid.

The invention claimed is:

1. An apparatus for extracorporeal removal of protein-bound toxins from blood plasma of a patient comprising
a first line device,
a second line device,
a third line device connectable to the patient,
a fourth line device connectable to the patient,
a blood purifier selected from the group consisting of a dialyzer, a hemofilter, an adsorber, and combinations thereof arranged between the first line device and the second line device,
a field generator at least partially surrounding the blood purifier, wherein the field generator is configured to generate (i) an electric DC field having a field strength of 10 V/m to 400 V/m or (ii) the electric DC field and at least one of a high frequency electric field having a frequency of 1 MHz to 200 MHz and a high frequency electromagnetic field having a frequency of 1 MHz to 200 MHz,
a controllable fluid conveyance device arranged in at least one of the first line device and the second line device for generating a controllable flow of fluid through the first and second line devices and the blood purifier,
at least one controllable body fluid conveyance unit arranged in at least one of the third line device and the fourth line device, and
a filter having a permeate side and a filtrate side, wherein the permeate side is connected to the first line device and the second line device, and the filtrate side has an inlet connected to the third line device and an outlet connected to the fourth line device.

2. The apparatus according to claim 1, wherein the field generator is configured to generate the high-frequency electromagnetic filed and the electric DC field.

3. The apparatus according to claim 1, wherein the field generator is configured to generate the high-frequency electric field and the electric DC field.

4. The apparatus according to claim 1, wherein the blood purifier is a dialyzer and an adsorber combination arranged between the first line device and the second line device.

5. The apparatus according to claim 1 for use in the treatment of acute or chronic renal failure.

6. The apparatus according to claim 1 for use in the treatment of acute or chronic hepatic failure.

7. An apparatus for extracorporeal removal of protein-bound toxins from blood plasma of a patient comprising
a first line device,
a second line device,
a third line device connectable to the patient,
a fourth line device connectable to the patient,
a blood purifier selected from the group consisting of a dialyzer, a hemofilter, an adsorber, and combinations thereof arranged between the first line device and the second line device,
a field generator at least partially surrounding the first line device and the blood purifier, wherein the field generator is configured to generate (i) an electric DC field having a field strength of 10 V/m to 400 V/m or (ii) the electric DC field and at least one of a high-frequency electric field having a frequency of 1 MHz to 200 MHz and a high-frequency electromagnetic field having a frequency of 1 MHz to 200 MHz,
a controllable fluid conveyance device arranged in at least one out of the first line device and the second line device for generating a controllable flow of fluid through the first and second line devices and the blood purifier,
at least one controllable body fluid conveyance unit arranged in at least one out of third line device or the fourth line device, and
a filter having a permeate side and a filtrate side, wherein the permeate side is connected to the first line device and the second line device, and wherein the filtrate side has an inlet connected to the third line device and an outlet connected to the fourth line device.

8. The apparatus according to claim 7, wherein the generator is selected from the group consisting of a high-frequency coil, a high-frequency electrode, a high-frequency capacitor, and combinations thereof.

9. The apparatus according to claim 7, wherein the blood purifier is a dialyzer and an adsorber combination arranged between the first line device and the second line device.

10. The apparatus according to claim 7, wherein the blood purifier is a dialyzer arranged between the first line device and the second line device.

11. The apparatus according to claim 7, wherein the blood purifier is an adsorber arranged between the first line device and the second line device.

12. The apparatus according to claim 7, wherein the field generator is configured to generate at least one of a high-frequency electric field having a frequency of 10 MHz to 200 MHz and a high-frequency electromagnetic field having a frequency of 10 MHz to 200 MHz.

13. The apparatus according to claim 7, wherein the field generator is configured to generate at least one of a high-frequency electric field having a frequency of 110 MHz to 113 MHz and a high-frequency electromagnetic field having a frequency of 110 MHz to 113 MHz.

\* \* \* \* \*